(12) United States Patent
Choi et al.

(10) Patent No.: US 11,185,666 B2
(45) Date of Patent: Nov. 30, 2021

(54) CATHETER DELIVERY DEVICE

(71) Applicants: THE ASAN FOUNDATION, Seoul (KR); UNIVERSITY OF ULSAN FOUNDATION FOR INDUSTRY COOPERATION, Ulsan (KR)

(72) Inventors: Jae Soon Choi, Seoul (KR); Young Jin Moon, Seoul (KR); Gi Byoung Nam, Seoul (KR); Young Hak Kim, Seoul (KR); Zhenkai Hu, Seoul (KR); Ho Yul Lee, Paju-si (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 235 days.

(21) Appl. No.: 16/530,167

(22) Filed: Aug. 2, 2019

(65) Prior Publication Data
US 2019/0351187 A1 Nov. 21, 2019

Related U.S. Application Data

(63) Continuation of application No. PCT/KR2018/001788, filed on Feb. 12, 2018.

(30) Foreign Application Priority Data
Mar. 8, 2017 (KR) .......................... 10-2017-0029637

(51) Int. Cl.
*A61M 25/01* (2006.01)
(52) U.S. Cl.
CPC ................. *A61M 25/0113* (2013.01)
(58) Field of Classification Search
CPC .......... A61M 25/0113; A61M 25/0125; A61M 2025/0166; A61M 25/01; A61M 25/0116;
(Continued)

(56) References Cited

U.S. PATENT DOCUMENTS

| | | | | |
|---|---|---|---|---|
| 5,188,612 A | * | 2/1993 | Herrington, Jr. | A61M 25/0631 600/576 |
| 7,435,230 B2 | | 10/2008 | Okada | |
| 2004/0249411 A1 | * | 12/2004 | Suzuki | A61B 17/29 606/205 |
| 2007/0179472 A1 | * | 8/2007 | Whittaker | A61M 25/013 604/528 |

(Continued)

FOREIGN PATENT DOCUMENTS

| | | |
|---|---|---|
| EP | 2 567 670 A1 | 3/2013 |
| EP | 2 875 792 A1 | 5/2015 |

(Continued)

OTHER PUBLICATIONS

International Search Report issued in PCT/KR2018/001788; dated May 21, 2018.

(Continued)

*Primary Examiner* — Kevin C Sirmons
*Assistant Examiner* — Antarius S Daniel
(74) *Attorney, Agent, or Firm* — Studebaker & Brackett PC

(57) ABSTRACT

A catheter delivery device having an improved mechanism for inserting a catheter into a blood vessel of a patient. The catheter delivery device includes at least: a body including a delivery path of a catheter; a pair of feeders having grippers located on the delivery path of the body and are configured to grip and release the catheter; and a rotator configured to rotate the catheter gripped by the feeders. The feeders move from a grip position where the grippers grip the catheter to a forward position where the grippers advance in a state of gripping the catheter, from the forward position to a grip release position where the grippers release the catheter, from the grip release position to a backward position where the grippers retract in a state of releasing a (Continued)

grip on the catheter, and from the backward position to the grip position.

19 Claims, 12 Drawing Sheets

(58) Field of Classification Search
CPC .............. A61B 2034/301; A61B 34/30; A61B 2017/00778; A61B 2017/00292
See application file for complete search history.

(56) References Cited

U.S. PATENT DOCUMENTS

| | | |
|---|---|---|
| 2008/0064920 A1 | 3/2008 | Bakos et al. |
| 2014/0276042 A1* | 9/2014 | Smith ................ A61M 5/14232 600/433 |
| 2014/0276939 A1* | 9/2014 | Kokish .............. A61M 25/0113 606/130 |
| 2015/0094732 A1* | 4/2015 | Pacheco ................. A61B 34/30 606/108 |
| 2015/0297864 A1 | 10/2015 | Kokish et al. |
| 2016/0354582 A1 | 12/2016 | Yu et al. |

FOREIGN PATENT DOCUMENTS

| | | |
|---|---|---|
| JP | 4354216 B2 | 10/2009 |
| JP | 2015-512746 A | 4/2015 |
| JP | 5723766 B2 | 5/2015 |
| WO | 2007/008967 A2 | 1/2007 |
| WO | 2014/093457 A1 | 6/2014 |

OTHER PUBLICATIONS

The extended European search report issued by the European Patent Office dated Feb. 13, 2020, which corresponds to European Patent Application No. 18763826.7-1115 and is related to U.S. Appl. No. 16/530,167.

* cited by examiner

CATHETER DELIVERY DEVICE

CROSS-REFERENCE TO RELATED APPLICATIONS

The present application is a continuation of International Patent Application No. PCT/KR2018/001788, filed Feb. 12, 2018, which is based upon and claims the benefit of priority to Korean Patent Application No. 10-2017-0029637, filed on Mar. 8, 2017. The disclosures of the above-listed applications are hereby incorporated by reference herein in their entirety.

BACKGROUND

Embodiments of the inventive concept described herein relate to a catheter delivery device, and more particularly, relate to a catheter delivery device for accurately performing catheterization by automatically inserting a catheter into a blood vessel of a patient and rotating the catheter.

Catheterization is widely used to treat arrhythmia or blood vessel diseases.

Accordingly, the introduction of a robot system is required to reduce catheterization time and accurately perform the catheterization.

Furthermore, an X-ray has to be taken during the catheterization to locate a catheter inserted into a human body.

However, a doctor and his/her team participating in the catheterization are always exposed to radiation by X-rays, and therefore all processes of the catheterization are required to be remotely performed.

Meanwhile, to smoothly insert an Electro-Physiology (EP) catheter, which is widely used to treat arrhythmia in the related art, into a blood vessel of a patient, a person has to push the tip of the catheter into the blood vessel, or rotate the catheter, with the person's hands.

As described above, in the related art, the person inserts the catheter into the blood vessel by holding the catheter with the person's hands and pushing or rotating the catheter. Therefore, the person fails to accurately identify the depth of the catheter inserted, which leads to deterioration in the accuracy of the catheterization. Accordingly, development of a device for accurately feeding a catheter is required.

Furthermore, a device for feeding a catheter should not slip on the catheter to accurately identify the depth of the catheter inserted, and has to be implemented to allow the catheter to be easily attached and controlled, such that the device easily switches between manual catheterization and automatic catheterization to easily cope with emergency situations.

SUMMARY

Embodiments of the inventive concept provide a catheter delivery device for easily inserting and removing a catheter, accurately identifying the depth of the catheter inserted, and improving the accuracy of catheterization.

According to some embodiments, a catheter delivery device includes a body including a delivery path of a catheter; a pair of feeders having grippers located on the delivery path of the body and are configured to grip and release the catheter; and a rotator configured to rotate the catheter gripped by the feeders. The feeders move from a grip position where the grippers grip the catheter to a forward position where the grippers advance in a state of gripping the catheter, from the forward position to a grip release position where the grippers release the catheter, from the grip release position to a backward position where the grippers retract in a state of releasing a grip on the catheter, and from the backward position to the grip position.

BRIEF DESCRIPTION OF DRAWINGS

The above and other objects and features will become apparent from the following description with reference to the following figures, wherein like reference numerals refer to like parts throughout the various figures unless otherwise specified, and wherein.

DETAILED DESCRIPTION

Figure 1:
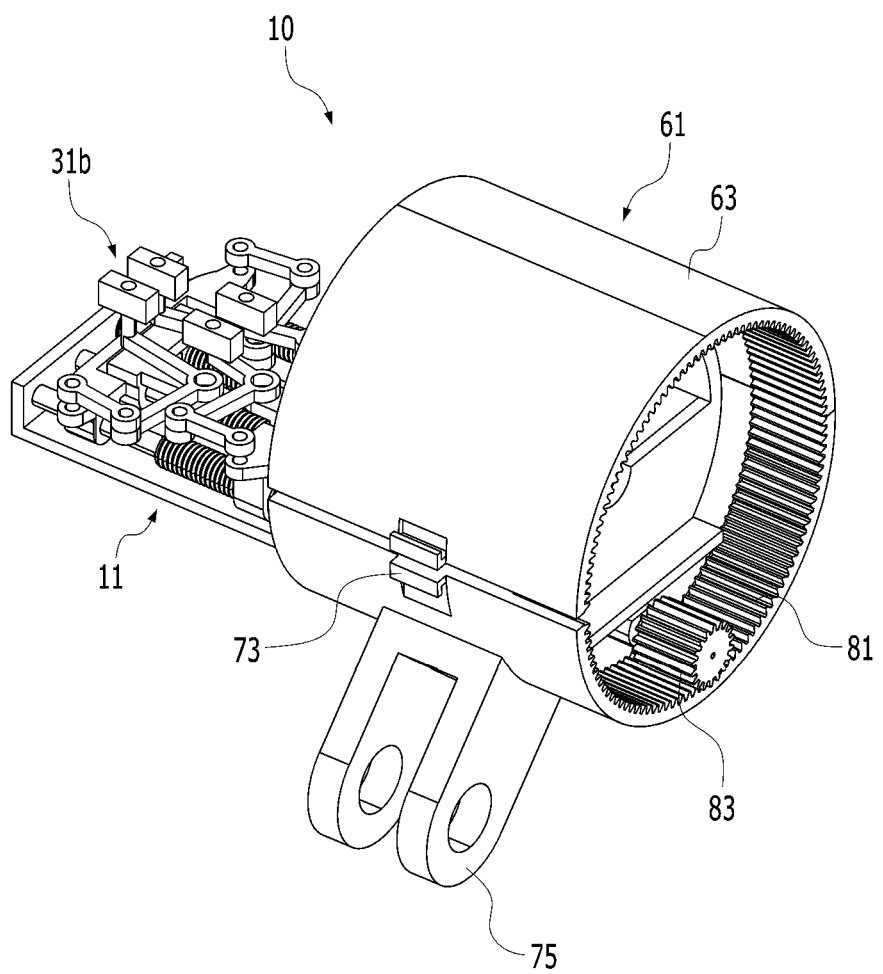
FIG. 1 is a perspective view of a catheter delivery device according to some embodiments of the present disclosure.
Figure 2:
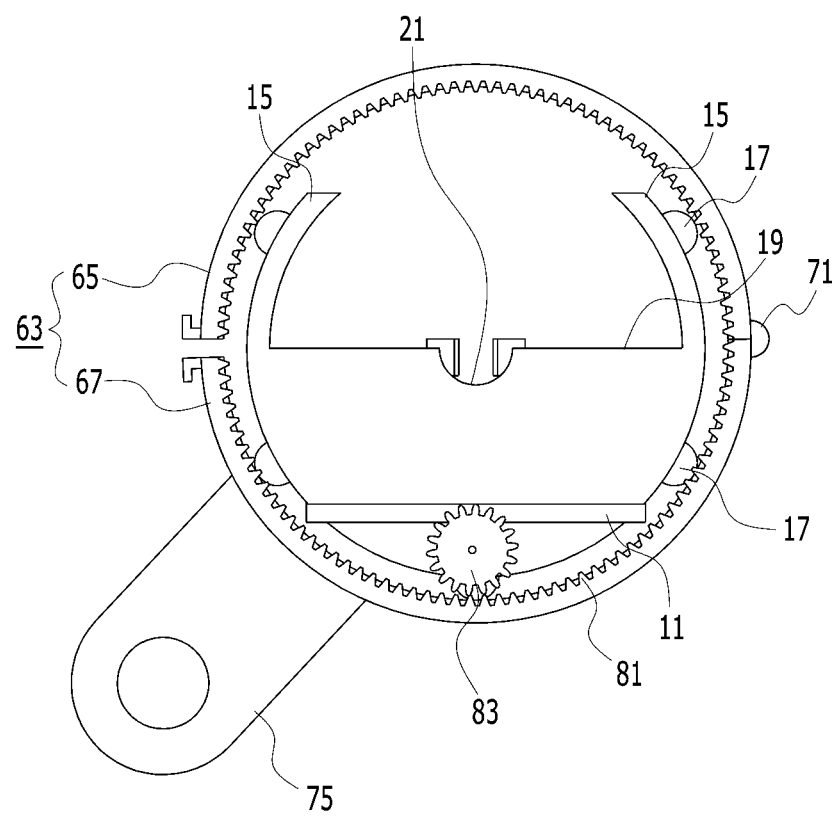
FIG. 2 is a right-side view of the catheter delivery device shown in FIG. 1.
Figure 3:
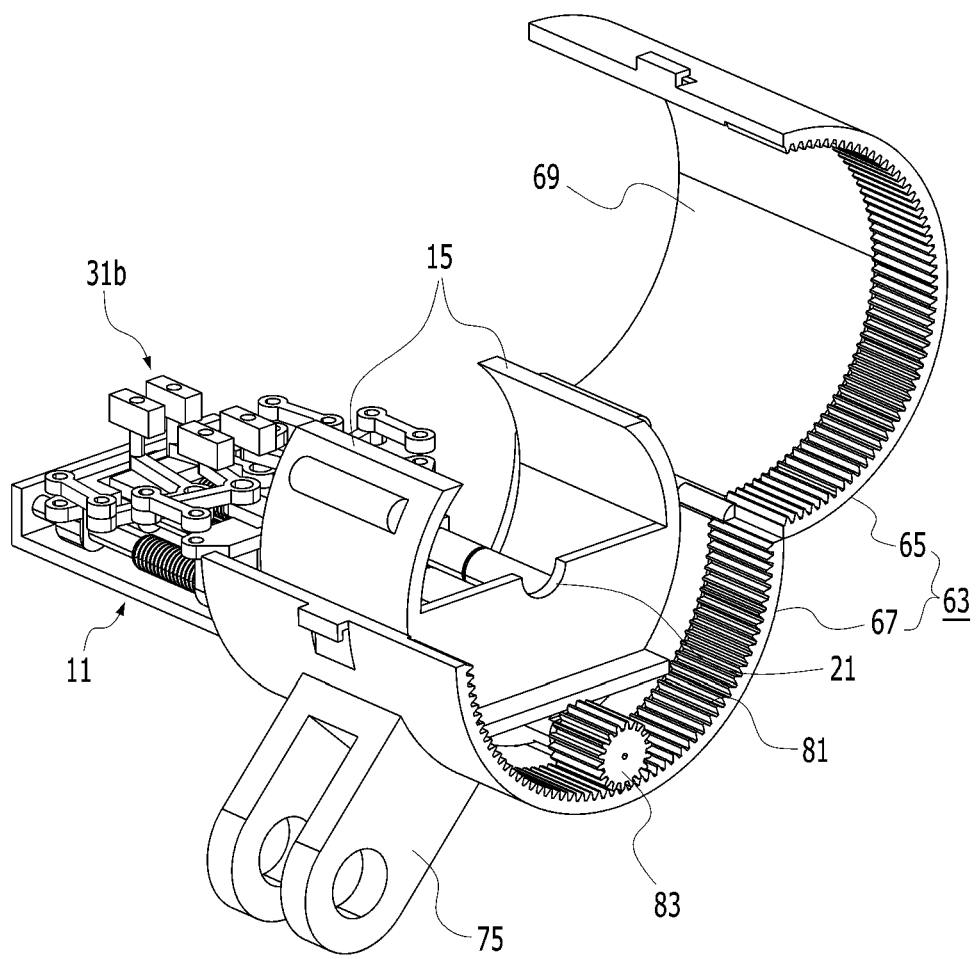
FIG. 3 is a perspective view illustrating a state in which an upper housing of the catheter delivery device shown in FIG. 1 is open.
Figure 4:
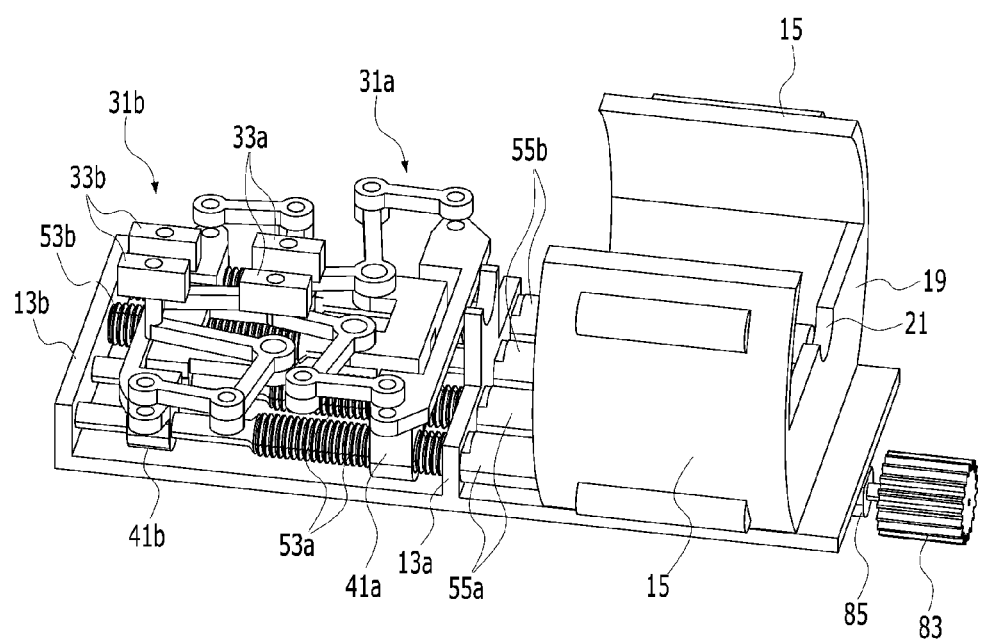
FIG. 4 is an enlarged perspective view of the pair of feeders of the catheter delivery device shown in FIG. 1.
Figure 5:
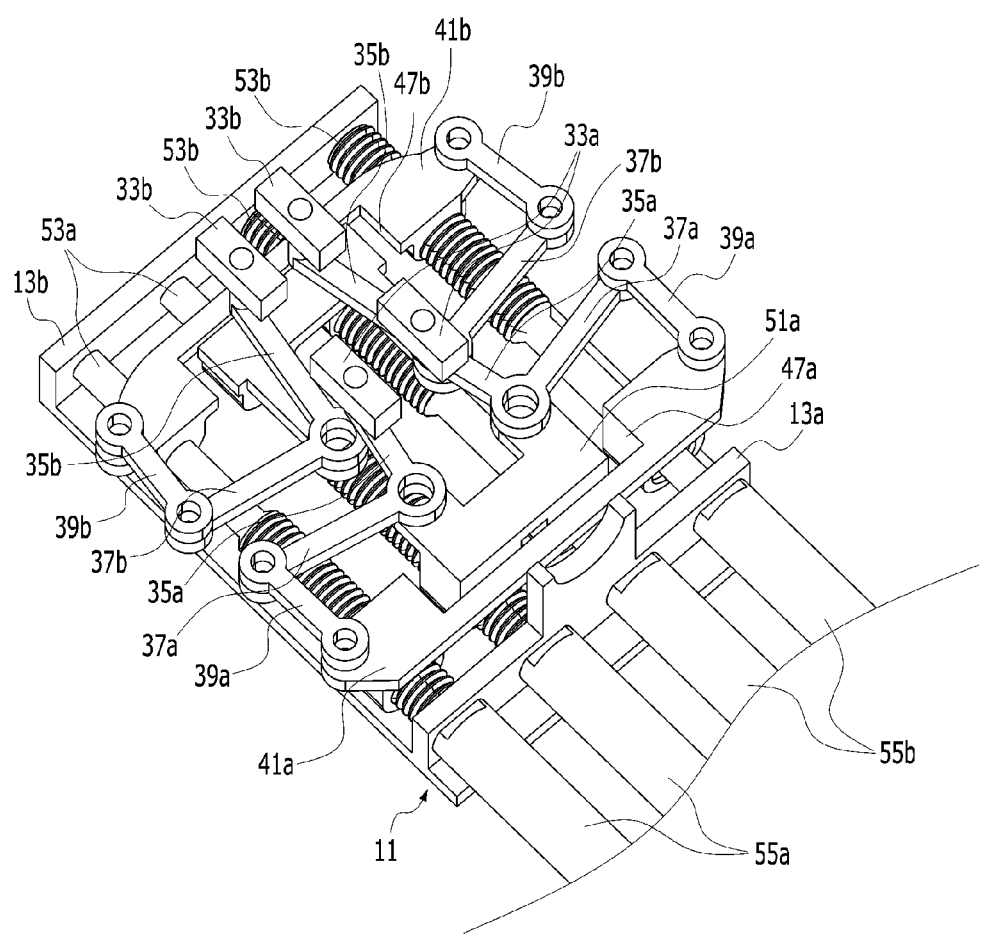
FIG. 5 is a further enlarged perspective view of the pair of feeders of the catheter delivery device shown in FIG. 1.
Figure 6:
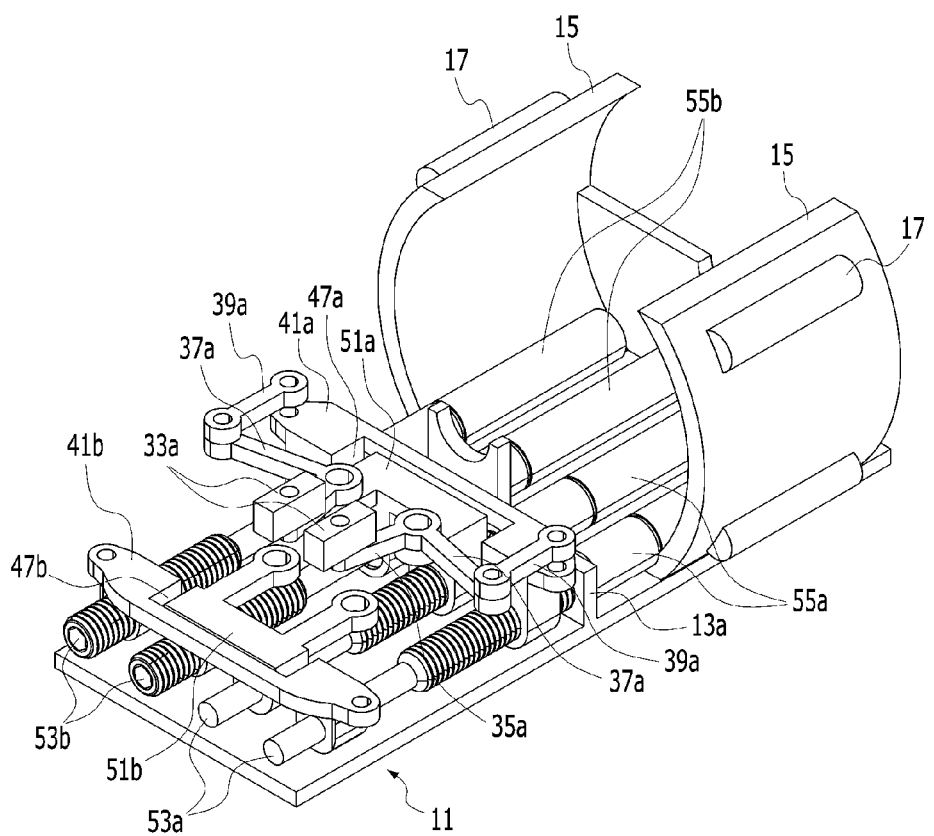
FIG. 6 is a perspective view illustrating a state in which a front feeder of the catheter delivery device shown in FIG. 4 is partly removed.
Figure 7:
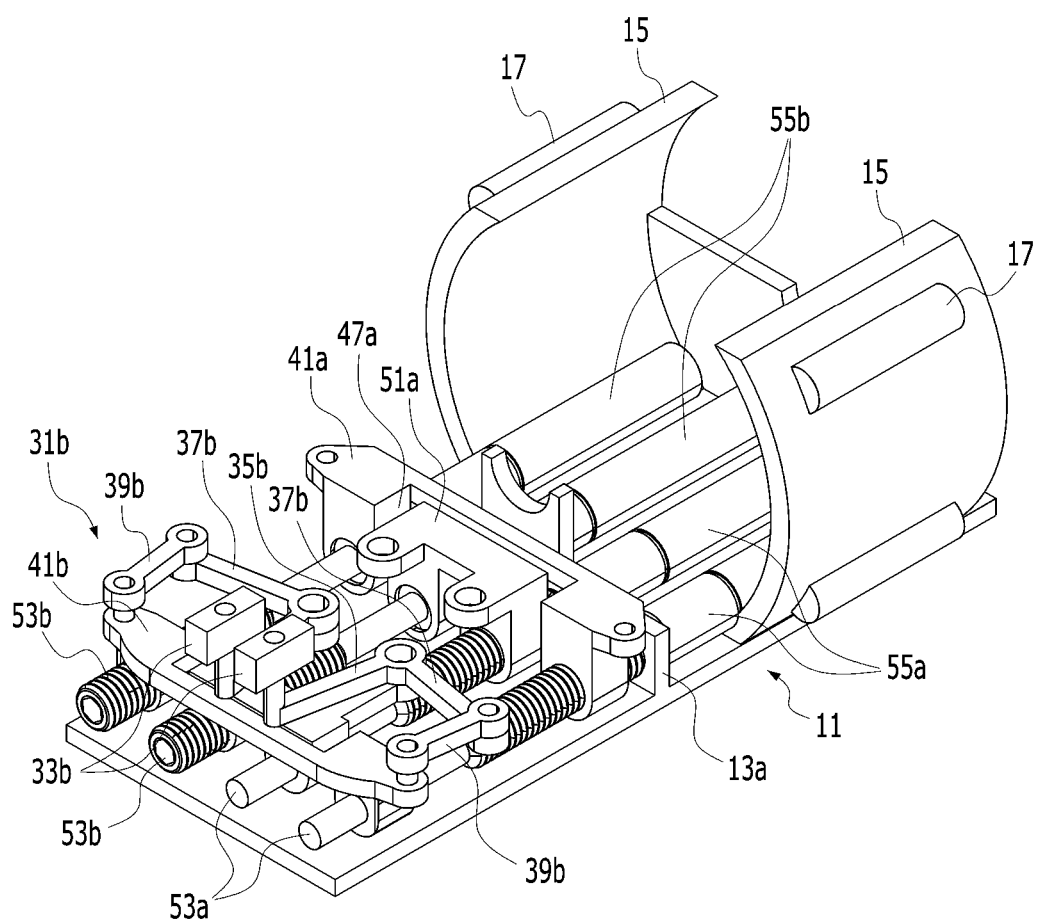
FIG. 7 is a perspective view illustrating a state in which a rear feeder of the catheter delivery device shown in FIG. 4 is partly removed.

The above and other aspects, features, and advantages of the inventive concept will become apparent from the following description of embodiments given in conjunction with the accompanying drawings. However, the inventive concept is not limited to the embodiments disclosed herein and may be implemented in various different forms. Herein, the embodiments are provided to provide complete disclosure of the inventive concept and to provide a thorough understanding of the inventive concept to those skilled in the art to which the inventive concept pertains, and the scope of the inventive concept should be limited only by the accompanying claims and equivalents thereof.

Terms used herein are only for descriptions of embodiments and are not intended to limit the inventive concept. As used herein, the singular forms are intended to include the plural forms as well, unless a context clearly indicates otherwise. It will be further understood that the terms "comprise" and/or "comprising" specify the presence of stated features, components, and/or operations, but do not preclude the presence or addition of one or more other features, components, and/or operations. In addition, identical numerals will denote identical components throughout the specification, and the meaning of "and/or" includes each mentioned item and every combination of mentioned items. It will be understood that, although the terms first, second, etc. may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should not be interpreted in an idealized or overly formal sense unless expressly so defined herein.

Hereinafter, the inventive concept will be described in detail with reference to the accompanying drawings.

Prior to the description, it should be noted that components having the same configurations in various embodiments are denoted by identical reference numerals and representatively described in some embodiments and only components different from those in the some embodiments are described in the some other embodiments.

Catheter delivery devices according to some embodiments of the present disclosure are illustrated in FIGS. 1 to 8.

As illustrated in the drawings, the catheter delivery device 10 according to some embodiments of the present disclosure includes a body 11, a pair of feeders 31a and 31b, and a rotator 61.

In some embodiments, the body 11 has a rectangular plate shape, and a delivery path along which a catheter 1 (e.g., shown in FIG. 8) moves is formed on the body 11. The pair of feeders 31a and 31b are disposed on one side of the body 11, and the rotator 61 is disposed on an opposite side of the body 11.

In some embodiments, the catheter delivery device 10 further includes a pair of threaded shaft supports 13a and 13b that rotatably support threaded shafts 53a and 53b of the pair of feeders 31a and 31b, which are further described below. The pair of threaded shaft supports 13a and 13b are provided on one side of a plate surface of the body 11, for example, on one side of an upper surface of the body 11. The pair of threaded shaft supports 13a and 13b are disposed with an interval therebetween across the lengthwise direction of the body 11. This description, as an example, describes the threaded shaft support located adjacent to the rotator 61 as the first threaded shaft support 13a, and the threaded shaft support located on the opposite side to the rotator 61 as the second threaded shaft support 13b. Here, the pair of threaded shafts 53a and 53b include a threaded shaft portion on which an external male thread for transmitting a rotational force is formed along the lengthwise direction and a sliding rod portion for linear motion. For example, the threaded shafts 53a of the rear feeder 31a include a threaded shaft portion at the rear thereof and a sliding rod at the front thereof. The threaded shafts 53a transmit power to a first movable block 51a and a second movable block 41a of the rear feeder 31a and allow a first movable block 51b and a second movable block 41b of the front feeder 31b to slide without the transmission of power. Accordingly, in these embodiments, a separate linear guide is unnecessary, and thus the number of parts is reduced.

In some embodiments, the catheter delivery device 10 further includes a pair of branches 15 having a circular arc shape and protruding upward from the body 11. The pair of branches 15 face each other and formed on an opposite side of the plate surface of the body 11, for example, on an opposite side of the upper surface of the body 11. Each of the branches 15 includes a plurality of rollers 17 provided thereon, which have an interval therebetween and are capable of rolling. The rollers 17 support the body 11 from an inner circumferential surface of a housing 63 of the rotator 61, which are further described below. The rollers 17 move in rolling contact with the inner circumferential surface of the housing 63.

End portions of the pair of branches 15 located adjacent to the rotator 61 are connected by a connecting plate 19, and a catheter mounting hole 21 in which the catheter 1 is movably mounted is formed through the connecting plate 19.

In some embodiments, the catheter delivery device 10 further includes a pair of feeders 31a and 31b having grippers 33a and 33b that are located on the delivery path of the catheter 1, on the body 11. The grippers 33a and 33b grip and release the catheter 1. The grippers 33a and 33b of the pair of feeders 31a and 31b are disposed with an interval therebetween along the delivery path of the catheter 1. The pair of feeders 31a and 31b feed the catheter 1 by mutually organically being moved to be placed in among a grip position where the grippers 33a and 33b grip the catheter 1, a forward position where the grippers 33a and 33b advance in the state in which the grippers 33a and 33b grip the catheter 1, a grip release position where the grippers 33a and 33b release the grip on the catheter 1, and a backward position where the grippers 33a and 33b retract in the state in which the grippers 33a and 33b release the grip on the catheter 1.

Hereinafter, this description, as an example, describes the feeder located adjacent to the rotator 61 as the rear feeder 31a, and the feeder located far away from the rotator 61 as the front feeder 31b. Furthermore, the rear feeder 31a and the front feeder 31b have the same components, and therefore specific descriptions of the components of the front feeder 31b are given by using the rear feeder 31a. The front feeder 31b is different from the rear feeder 31a in terms of an arrangement of some components, and the difference are further described below.

Hereinafter, a feeding process of the catheter 1 according to operations of the pair of feeders 31a and 31b are also further described below.

The rear feeder 31a includes the pair of grippers 33a, a pair of gripper links 35a, a pair of first links 37a, a pair of second links 39a, the second movable block 41a, the first movable block 51a, the pair of threaded shafts 53a, and a pair of threaded shaft drive motors 55a. Here, according to some embodiments, the pair of gripper links 35a and the pair of first links 37a are implemented with one part to form a specific fixed angle. Here, according to some embodiments, the catheter 1 advances or retracts when the second movable block 41a and the first movable block 51a advance or retract at the same speed. Furthermore, the grippers 33a are closed when the second movable block 41a moves faster than the first movable block 51a, and the grippers 33a are opened when the second movable block 41a moves slower than the first movable block 51a.

The pair of grippers 33a are arranged in parallel along the delivery path of the catheter 1 to face each other with the catheter 1 therebetween. In those embodiments, the pair of grippers 33a have a pad shape that is configured to closely contact with an outer circumferential surface of the catheter 1. In some embodiments, the grippers 33a include a material capable of increasing friction with the catheter 1. For example, the grippers 33a include rubber or silicone material.

The pair of gripper links 35a have a bar shape with a predetermined length and pivotally combine the pair of grippers 33a on opposite sides of the catheter 1. One end portion of each gripper link 35a is pivotally coupled to the gripper 33a, and an opposite end portion of the gripper link 35a is fixed to the first link 37a at a particular angle and pivotally coupled to the first movable block 51a. The gripper link 35a is disposed toward the rotator 61. In these embodiments, the gripper link 35a is integrally formed with the first link 37a while forming the particular angle with the first link 37a.

The points to which the pair of first links 37a and the pair of gripper links 35a are fixed are pivotally coupled to the first movable block 51a, and an opposite end portion of each first link 37a is pivotally coupled to the second link 39a.

The pair of second links 39a have a bar shape with a predetermined length. One end portion of each second link 39a is pivotally coupled to the first link 37a, and an opposite end portion of the second link 39a is pivotally coupled to the second movable block 41a.

In these embodiments, all the components, for example, the grippers 33a, the links 35a, 37a, and 39a, the first movable block 51a, the second movable block 41a, the body 11, and the threaded shafts 53a, except the threaded shaft drive motors 55a only include non-magnetic and non-metal materials.

In some embodiments as shown in the figures of the present disclosure, the second movable block 41a has a rectangular block shape and is disposed across the delivery path of the catheter 1. The pair of second links 39a are pivotally coupled to opposite end portions of the second movable block 41a, respectively. Furthermore, the second movable block 41a has a through-hole (not illustrated) into which one threaded shaft 53a of the rear feeder 31a is threaded to transmit power by rotation of the threaded shaft 53a and a through-hole (not illustrated) through which the unthreaded portion, for example, the sliding rod portion of one threaded shaft 53b of the front feeder 31b is coupled. In those embodiments, the second movable block 41a of the rear feeder 31a is driven in the direction parallel to the catheter 1 by receiving power through the threaded shaft 53a and simultaneously performing sliding motion with the threaded shaft 53b of the front feeder 31b. Based on the structure described above, a separate linear guide for guiding a linear movement of the second movable block 41a is not required. In some embodiments, a block receiving portion 47a in which the first movable block 51a is partly received is concavely formed in the central region of the second movable block 41a. The block receiving portion 47a is concavely formed toward the rotator 61.

In some embodiments, the first movable block 51a has a through-hole (not illustrated) that has an internal female thread formed therein and into which the threaded shaft 53a is threaded to perform screw motion, and a through-hole (not illustrated) through which the sliding rod portion of the threaded shaft 53b is coupled. The pair of gripper links 35a are pivotally coupled to the first movable block 51a.

In some embodiments, the pair of threaded shafts 53a have a rod shape with a predetermined length and are arranged parallel to the delivery path of the catheter 1. The pair of threaded shafts 53a are rotatably supported by the pair of threaded shaft supports 13a and 13b. Furthermore, the pair of threaded shafts 53a are threaded into the second movable block 41a to perform screw motion. The pair of threaded shafts 53a rectilinearly reciprocate the first movable block 51a and the second movable block 41a along the delivery path of the catheter 1.

In some embodiments, the pair of threaded shaft drive motors 55a are directly coupled to the respective threaded shafts 53a and rotate the respective threaded shafts 53a in clockwise direction and counterclockwise direction. The threaded shaft drive motors 55a are supported in parallel by the first threaded shaft support 13a disposed adjacent to the rotator 61. In those embodiments, the grippers 33a perform opening or closing motion when revolutions per minute (RPM) of the pair of threaded shaft drive motors 55a differ from each other, and perform reciprocating motion while remaining in the current state when the RPMs of the pair of threaded shaft drive motors 55a are the same as each other.

Accordingly, for example, when the threaded shaft drive motors 55a are rotated in one direction, the threaded shafts 53a rotate in the one direction, and the first movable block 51a and the second movable block 41a advance away from the rotator 61 by screw motion of the threaded shafts 53a, the first movable block 51a, and the second movable block 41a. The grippers 33a grip and advance the catheter 1 by mutual joint motion between the links in the state of being spaced apart from the catheter 1 and insert the catheter 1 into a blood vessel of a patient.

In a different example, which is contrast to the above example, when the threaded shaft drive motors 55a are rotated in an opposite direction, the threaded shafts 53a rotate in the opposite direction, and the second movable block 41a retracts to approach the rotator 61 by screw motion of the threaded shafts 53a, the first movable block 51a, and the second movable block 41a. By mutual joint motion between the links, the grippers 33a gripping the catheter 1 move away from the catheter 1 and retract in the state of not gripping the catheter 1.

The catheter 1 is fed along the delivery path of the catheter 1 and inserted into the blood vessel of the patient, by the series of above actions.

In some embodiments, the grippers 33a and the gripper links 35a, the gripper links 35a and the first movable block 51a, the first links 37a and the second links 39a, and the second links 39a and the second movable block 41a are pivotally coupled with each other by pins (not illustrated in the figures in the present disclosure).

Meanwhile, in some embodiments, the front feeders 31b of the catheter delivery device 10 according to the some embodiments of the present disclosure differs from the rear feeders 31a in that the grippers 33b and the second movable block 41b are disposed adjacent to the second threaded shaft support 13b. Furthermore, in some embodiments, the first movable block 51a and the second movable block 41b of the front feeders 31b have through-holes (not illustrated) through which the pair of threaded shafts 53b are coupled and through-holes (not illustrated) through which the sliding rod portions of the pair of threaded shafts 53a of the rear feeders 31a are coupled.

In some embodiments, internal female threads into which the threaded shafts 53b are threaded to perform screw motion are formed in the through-holes of the first and second movable blocks 51a and 41b through which the pair of threaded shafts 53b of the front feeders 31b pass. Further, a block receiving portion 47b in which the first movable block 51a is partly received is concavely formed in the central region of the second movable block 41b. The block receiving portion 47b is concavely formed toward the opposite side to the rotator 61. Accordingly, in some embodiments, the first movable block 51b of the front feeders 31b and the first movable block 51a of the rear feeders 31a are disposed to face each other.

Furthermore, likewise to the threaded shaft drive motors 55a of the rear feeders 31a, a pair of threaded shaft drive motors 55b of the front feeders 31b are supported in parallel by the first threaded shaft support 13a.

In the present disclosure, reference numeral 35b denotes gripper links of the front feeders 31b, reference numeral 37b denotes first links of the front feeders 31b, and reference numeral 39b denotes second links of the front feeders 31b.

As described above, in the catheter delivery device 10 according to the some embodiments of the present disclosure, the grippers 33b, the links 35b, 37b, and 39b, the first movable block 51a, and the second movable block 41b of the front feeders 31b and the grippers 33a, the links 35a, 37a, and 39a, the movable block 41a, and the support block 51a of the rear feeders 31a are disposed between the pair of threaded shaft supports 13a and 13b of the body 11 to form a catheter placer 301 for feeding and inserting the catheter 1 into the blood vessel of the patient.

In some embodiments, although not illustrated in the figures of the present disclosure, the front feeders 31b and the rear feeders 31a are disposed to cover each other while forming layers, thereby reducing the interval between the pair of threaded shaft supports 13a and 13b and thus reducing the entire length of the catheter delivery device 10 to achieve compactness of the catheter delivery device 10.

In some embodiments, the rotator 61 rotates the catheter 1 gripped by at least one of the pair of feeders 31a and 31b. The rotator 61 includes the housing 63, an inner gear 81, a pinion 83, and a pinion drive motor 85. In some embodiments, the housing 63 has a hollow cylindrical shape and receives a portion of the body 11 therein. In some embodiments, the housing 63 has a track 69 formed on one side of the inner circumferential surface thereof, and the plurality of rollers 17 of the body 11 are supported on the track 69 and move in rolling contact with the track 69.

Meanwhile, the housing 63 in these embodiments includes an upper housing 65 and a lower housing 67 divided from each other in the vertical direction. One end portion of the upper housing 65 and one end portion of the lower housing 67 are hinged to each other by a hinge pin, and an opposite end portion of the upper housing 65 and an opposite end portion of the lower housing 67 are locked by a locking device 73.

Accordingly, in some embodiments, when the locking device 73 is unlocked and the upper housing 65 is rotated upward with respect to the lower housing 67, the upper housing 65 is rotated about the hinge pin to open a region of the body 11. In contrast, when the upper housing 65 is rotated downward with respect to the lower housing 67 and locked by the locking device 73, the region of the body 11 is covered without being exposed to the outside. Accordingly, in some embodiments, the upper housing 65 is opened to simply and conveniently mount the catheter 1 on the delivery path of the catheter 1 above the body 11 or to simply and conveniently remove the catheter 1 from the delivery path of the catheter 1.

Furthermore, in some embodiments, a fixing part 75 for fixing the housing 63 to a structure is provided on the outside of the housing 63. Accordingly, in some embodiments, the catheter delivery device 10 is stably used by fixing the catheter delivery device 10 to a structure, such as a separate robot arm or a bed support, through the fixing part 75.

In some embodiments, the inner gear 81 includes a plurality of gear teeth formed on a region of the inner circumferential surface of the housing 63, for example, on an opposite side of the inner circumferential surface of the housing 63. Accordingly, in some embodiments, the inner gear 81 has a ring gear shape.

In some embodiments, the pinion 83 has the shape of an outer gear that includes gear teeth having the same shape and size as the gear teeth of the inner gear 81. The pinion 83 is configured to be engaged with the gear teeth of the inner gear 81 to rotate.

In some embodiments, the pinion drive motor 85 is directly coupled with the pinion 83 and rotates the pinion 83 in clockwise direction and counterclockwise direction. The pinion drive motor 85 is supported on a bottom surface of the body 11 received in the housing 63.

Accordingly, when the pinion drive motor 85 is rotated in one direction or an opposite direction in the state in which the grippers 33a, 33b of at least one of the pair of feeders 31a and 31b grip the catheter 1, the rotational force of the pinion drive motor 85 is transmitted to the pinion 83, the pinion 83 rotates in one direction or an opposite direction along the inner gear 81, and the catheter 1 rotates in the one direction or the opposite direction at the same time that the body 11 rotates in the one direction or the opposite direction.

Hereinafter, a process of feeding the catheter 1 using the above-configured catheter delivery device 10 according to the some embodiments of the present disclosure is further described. In such description, a movement of the grippers 33a and 33b or the movable blocks 41a and 41b in the direction away from the rotator 61 is referred to as a forward movement, and a movement of the grippers 33a and 33b or the movable blocks 41a and 41b toward the rotator 61 is referred to as a backward movement.

Figure 8:
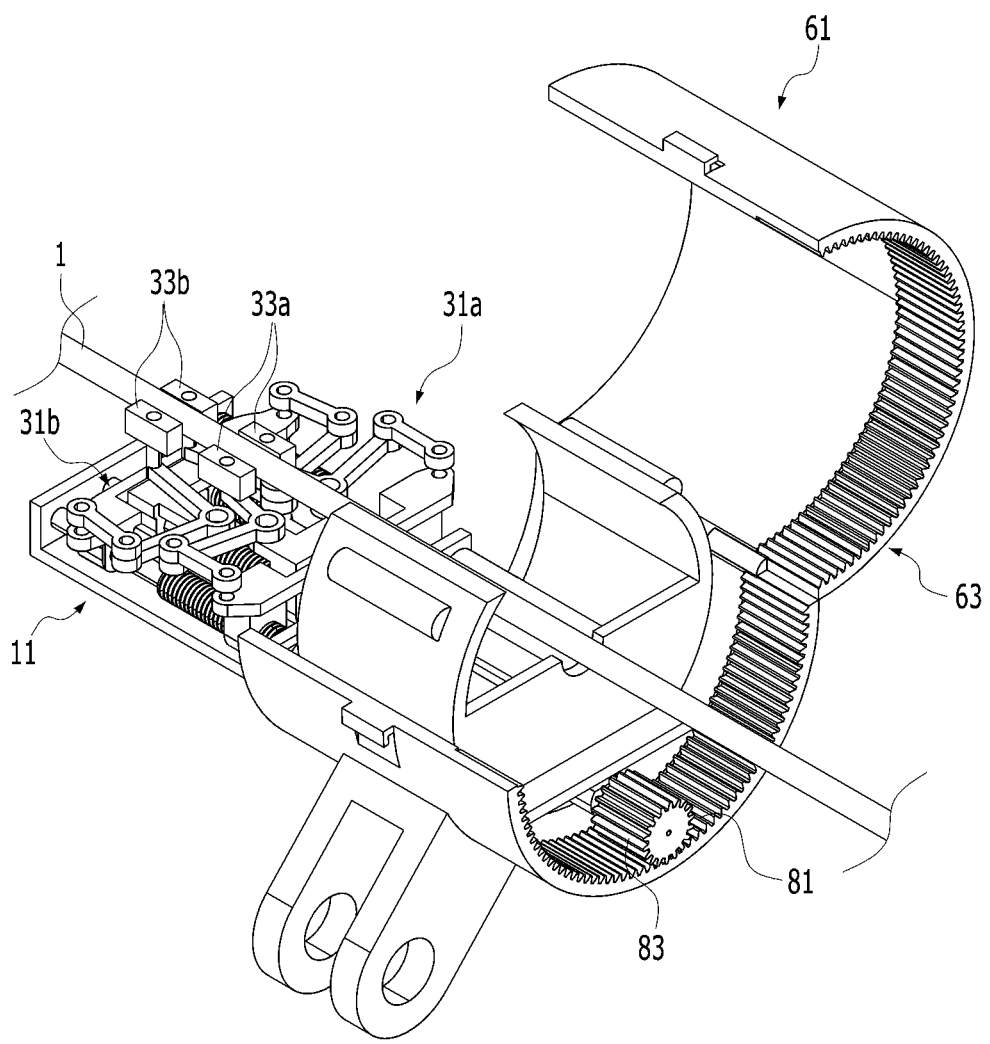
FIG. 8 is a view illustrating a state in which a catheter is mounted while the upper housing of the catheter delivery device shown in FIG. 1 is open.

First, as illustrated in FIG. 8 of the drawings, the upper housing 65 is opened, and the catheter 1 is disposed on the body 11 along the delivery path of the catheter 1 formed between the pair of grippers 33b of the front feeders 31b and the pair of grippers 33a of the rear feeders 31a and is mounted in the catheter mounting hole 21 of the body 11. At this stage, the pair of grippers 33b of the front feeders 31b and the pair of grippers 33a of the rear feeders 31a does not grip the catheter 1.

Next, the upper housing 65 is locked to the lower housing 67 through the locking device 73 to cover a region of the body 11. At this stage, the upper housing 65 and the lower housing 67 form a single ring shape, and the body 11 is supported on the inner circumferential surface of the housing 63 by the plurality of rollers 17.

Then, in a first step, when the threaded shaft drive motors 55b screwed into the second movable block 41b of the front feeders 31b are rotated forward in one direction, the second movable block 41b advances by screw motion between the threaded shafts 53b and the second movable block 41b, and the pair of grippers 33b advance together with the second movable block 41b by mutual joint motion between the links and are located in the grip position where the grippers 33b grip the catheter 1.

In a second step, when the threaded shaft drive motors 55b of the front feeders 31b are rotated forward in the one direction, the first movable block 51b and the second movable block 41b advance by screw motion between the threaded shafts 53b, the first movable block 51b, and the second movable block 41b, and the pair of grippers 33b are located in the forward position, where the grippers 33b advance by mutual joint motion between the links, in the state of gripping the catheter 1.

In this second step, when the threaded shaft drive motors 55a of the rear feeders 31a are rotated backward in an opposite direction, the first movable block 51a and the second movable block 41a retract by screw motion between the threaded shafts 53a, the first movable block 51a, and the second movable block 41a, and the pair of grippers 33a retract by mutual joint motion between the links in the state of not gripping the catheter 1 and are located in the backward position. Accordingly, the catheter 1 is advanced a predetermined distance by the front feeders 31b and inserted into a blood vessel of a patient, without being disturbed by the rear feeders 31a.

In a third step, when the threaded shaft drive motors 55b screwed into the second movable block 41b of the front feeders 31b are rotated backward in the opposite direction, the second movable block 41b retracts by screw motion between the threaded shafts 53b and the second movable block 41b, and the pair of grippers 33b retract together with the second movable block 41b by mutual joint motion between the links and are located in the grip release position where the grippers 33b release the grip on the catheter 1.

In this third step, when the threaded shaft drive motors 55a screwed into the second movable block 41a of the rear feeders 31a are rotated forward in the one direction, the second movable block 41a advances by screw motion between the threaded shafts 53a and the second movable block 41a, and the pair of grippers 33a advance together with the second movable block 41a by mutual joint motion between the links and are located in the grip position where the grippers 33a grip the catheter 1.

In a fourth step, when the threaded shaft drive motors 55b of the front feeders 31b are rotated backward in the opposite direction, the first movable block 51b and the second movable block 41b retract by screw motion between the threaded shafts 53b, the first movable block 51b, and the second movable block 41b, and the pair of grippers 33b retract by mutual joint motion between the links in the state of not gripping the catheter 1 and are located in the backward position.

In this fourth step, when the threaded shaft drive motors 55a of the rear feeders 31a are rotated forward in the one direction, the first movable block 51a and the second movable block 41a advance by screw motion between the threaded shafts 53a, the first movable block 51a, and the second movable block 41a, and the pair of grippers 33a are located in the forward position, where the grippers 33a advance by mutual joint motion between the links, in the state of gripping the catheter 1. Accordingly, the catheter 1 is advanced a predetermined distance by the rear feeders 31a and inserted into the blood vessel of the patient, without being disturbed by the front feeders 31b.

In a fifth step, when the threaded shaft drive motors 55b screwed into the second movable block 41b of the front feeders 31b are rotated forward in the one direction, the second movable block 41b advances by screw motion between the threaded shafts 53b and the second block 41b, and the pair of grippers 33b advance together with the second movable block 41b by mutual joint motion between the links and are located in the grip position where the grippers 33b grip the catheter 1.

In this fifth step, when the threaded shaft drive motors 55a screwed into the second movable block 41a of the rear feeders 31a are rotated forward in the opposite direction, the second movable block 41a retracts by screw motion between the threaded shafts 53a and the second movable block 41a, and the pair of grippers 33a retract together with the second movable block 41a by mutual joint motion between the links and are located in the grip release position where the grippers 33a do not grip the catheter 1.

When the fifth step is completed as described above, the catheter delivery device 10 returns to the second step and repeatedly performs the second to fifth steps. Accordingly, in these embodiments, the catheter delivery device 10 automatically feeds and inserts the catheter 1 into the blood vessel of the patient while mutually organically moving the pair of feeders 31a and 31b. Furthermore, in these embodiments, the catheter 1 is gripped by either the pair of grippers 33b of the front feeders 31b or the pair of grippers 33a of the rear feeders 31a.

Hereinafter, a process of rotating the catheter 1 using the catheter delivery device 10 according to the some embodiments of the present disclosure is further described.

When the pinion drive motor 85 is rotated in one direction in the state in which the grippers 33a, 33b of at least one of the pair of feeders 31a and 31b grip the catheter 1, the rotational force of the pinion drive motor 85 is transmitted to the pinion 83, the pinion 83 rotates along the inner gear 81, and the catheter 1 rotates in the one direction at the same time that the body 11 rotates in the one direction.

In contrast, when the pinion drive motor 85 is rotated in an opposite direction in the state in which the grippers 33a, 33b of at least one of the pair of feeders 31a and 31b grip the catheter 1, the rotational force of the pinion drive motor 85 is transmitted to the pinion 83, the pinion 83 rotates along the inner gear 81, and the catheter 1 rotates in the opposite direction at the same time that the body 11 rotates in the opposite direction.

In the catheter delivery device 10 according to some embodiments of the present disclosure, the operation of feeding the catheter 1 by the pair of feeders 31a and 31b and the operation of rotating the catheter 1 by the rotator 61 is performed separately or simultaneously.

As described above, the catheter delivery device 10 according to the some embodiments of the present disclosure accurately feeds the catheter 1 by allowing the pair of feeders 31a and 31b to mutually organically move among the grip position where the grippers 33a and 33b grip the catheter 1, the forward position where the grippers 33a and 33b advance in the state in which the grippers 33a and 33b grip the catheter 1, the grip release position where the grippers 33a and 33b release the grip on the catheter 1, and the backward position where the grippers 33a and 33b retract in the state in which the grippers 33a and 33b release the grip on the catheter 1.

Furthermore, the pair of grippers 33a, 33b of at least one of the feeders 31a and 31b always grip the catheter 1 after the catheter 1 is mounted on the catheter delivery device 10 according to some embodiments of the present disclosure. Accordingly, the depth of the catheter 1 inserted into the blood vessel of the patient may be accurately identified, and the accuracy of the catheterization would be improved.

Moreover, in the catheter delivery device 10 according to some embodiments of the present disclosure, the grippers 33a and 33b of the feeders 31a and 31b would release the grip on the catheter 1 without additional separate devices, and thus the catheter 1 would be easily separated from the catheter delivery device 10. Due to this operation, in an emergency situation during the catheterization, the catheter delivery device 10 is easily switched to a manual mode to allow an operator to directly manipulate the catheter 1 without using a surgical robot.

In addition, the catheter delivery device 10 would automatically smoothly insert the catheter 1 into the blood vessel of the patient while rotating the catheter 1 by operating the rotator 61 when necessary.

Meanwhile, the catheter inserted into the blood vessel of the patient would be automatically smoothly extracted by performing the above-described steps in the reverse order.

Figure 9:
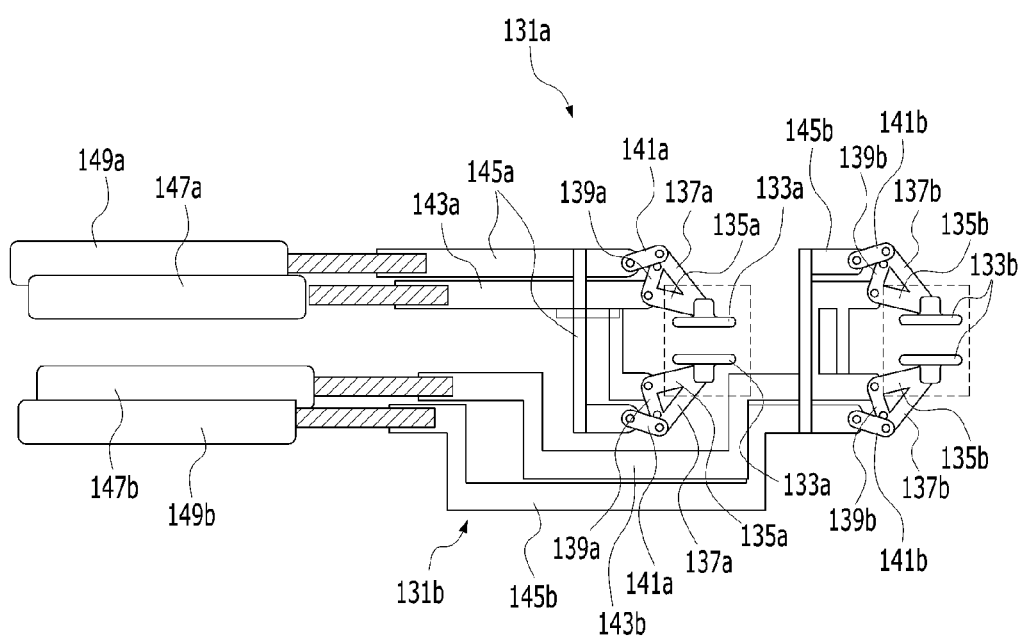
FIG. 9 is a view illustrating a configuration of a pair of feeders according to some embodiments of the present disclosure.

FIG. 9 illustrates a pair of feeders of a catheter delivery device according to some embodiments of the present disclosure.

According to some embodiments illustrated in FIG. 9, the feeders 131a and 131b are paired with each other. In this description related to FIG. 9, the feeders located adjacent to the rotator (not illustrated) are referred to as the rear feeders 131a, and the feeders located far away from the rotator is referred to as the front feeders 131b. Furthermore, because the rear feeders 131a and the front feeders 131b have the same components, the rear feeders 131a is representatively described, and descriptions of the components of the front feeders 131b is omitted.

The rear feeders 131a includes a pair of grippers 133a, a pair of first gripper links 135a, a pair of second gripper links 137a, a pair of connecting links 139a, a pair of auxiliary links 141a, a first drive rod 143a, a second drive rod 145a, a first linear driver 147a, and a second linear driver 149a.

The pair of grippers 133a are arranged in parallel along a delivery path of a catheter to face each other with the catheter therebetween. In these embodiments, the pair of grippers 133a have a pad shape that is configured to closely contact with an outer circumferential surface of the catheter. In these embodiments, the pair of first gripper links 135a, the pair of second gripper links 137a, and the pair of connecting links 139a form a triangle shape as a single part.

In these embodiments, the pair of first gripper links 135a have a bar shape with a predetermined length and pivotally combine the pair of grippers 133a on opposite sides of the catheter. One end portion of each first gripper link 135a is pivotally coupled to the gripper 133a, and an opposite end portion of the first gripper link 135a is pivotally coupled to the connecting link 139a and the first drive rod 143a. The gripper links 135a and 137a are disposed toward the rotator.

In these embodiments, the pair of second gripper links 137a have a bar shape with a predetermined length and are pivotally coupled to the pair of grippers 133a, respectively, while forming an angle with the pair of first gripper links 135a. One end portion of each second gripper link 137a is pivotally coupled to the gripper 133a, and an opposite end portion of the second gripper link 137a is fixed to the connecting link 139a while forming an angle with the connecting link 139a and is pivotally coupled to the auxiliary link 141a.

In these embodiments, the pair of connecting links 139a have a bar shape with a predetermined length and have a shape that is fixed to the pair of first gripper links 135a and the pair of second gripper links 137a to form a triangular shape with the pair of first gripper links 135a and the pair of second gripper links 137a. One end portion of each connecting link 139a is pivotally coupled to the first gripper link 135a and the first drive rod 143a, and an opposite end portion of the connecting link 139a is fixed to the second gripper link 137a at a specific angle and pivotally coupled to the auxiliary link 141a.

In these embodiments, the pair of auxiliary links 141a have a bar shape with a predetermined length and are pivotally coupled to the connecting link 139a and the second gripper link 137a. One end portion of each auxiliary link 141a is pivotally coupled to the second gripper link 137a and the connecting link 139a, and an opposite end portion of the auxiliary link 141a is pivotally coupled to the second drive rod 145a.

The first drive rod 143a is pivotally coupled to the pair of first gripper links 135a and the pair of connecting links 139a. The first linear driver 147a is directly connected to a free end portion of the first drive rod 143a.

The second drive rod 145a is pivotally coupled to the pair of auxiliary links 141a. The second linear driver 149a is directly connected to a free end portion of the second drive rod 145a.

The first linear driver 147a is connected to the first drive rod 143a and rectilinearly reciprocates the first drive rod 143a.

The second linear driver 149a is connected to the second drive rod 145a and rectilinearly reciprocates the second drive rod 145a. The second linear driver 149a is drivers 149a synchronized with the first linear driver 147a to allow the first drive rod 143a and the second drive rod 145a of the rear feeders 131a to rectilinearly move at the same speed. Here, the speeds of the first linear driver 147a and the second linear drivers 149a are synchronized with each other to move the grippers forward or backward. Furthermore, the grippers 133a are closed when the speed of the second linear drivers 149a is higher than the speed of the first linear drivers 147a, and the grippers 133a are opened when the speed of the second linear drivers 149a is lower than the speed of the first linear drivers 147a.

In some embodiments, the gripper 133a, the first gripper link 135a, and the second gripper link 137a are pivotally coupled by a pin (non-illustrated in the figures of the present disclosure), the coupling point of the first gripper link 135a, the connecting link 139a, and the first drive rod 143a are pivotally coupled by another pin (non-illustrated in the figures of the present disclosure), the second gripper link 137a, the connecting link 139a, and the auxiliary link 141a are pivotally coupled by a different pin (non-illustrated in the figures of the present disclosure), and the auxiliary link 141a and the second drive rod 145a are pivotally coupled by another different pin (non-illustrated in the figures of the present disclosure).

Among other reference numerals not described above, reference numeral 133b denotes grippers of the front feeders 131b, reference numeral 135b denotes first gripper links of the front feeders 131b, reference numeral 137b denotes second gripper links of the front feeders 131b, reference numeral 139b denotes connecting links of the front feeders 131b, and reference numeral 141b denotes auxiliary links of the front feeders 131b. Moreover, reference numeral 143b denotes a first drive rod of the front feeders 131b, reference numeral 145b denotes a second drive rod of the front feeders 131b, reference numeral 147b denotes a first linear driver of the front feeders 131b, and reference numeral 149b denotes a second linear driver of the front feeders 131b.

Hereinafter, a process of feeding the catheter using the above-configured pair of feeders 131a and 131b according to some other embodiments of the present disclosure is described First, in these embodiments, the upper housing 65 is opened, and the catheter is disposed on the body 11 along the delivery path of the catheter formed between the pair of grippers 133b of the front feeders 131b and the pair of grippers 133b of the rear feeders 131a and is mounted in the catheter mounting hole 21 of the body 11. At this stage, the pair of grippers 133b of the front feeders 131b and the pair of grippers 133a of the rear feeders 131a do not grip the catheter.

Next, the upper housing 65 is locked to the lower housing 67 through the locking device 73 to cover a region of the body 11.

Then, in a first step of these embodiments, when the second drive rod 145b is advanced by driving the second linear drivers 149b connected to the second drive rod 145b of the front feeders 131b, the pair of grippers 133b gripping the catheter advance a predetermined distance by mutual joint motion between the links, and the pair of grippers 133b are located in a grip position where the grippers 133b grip the catheter.

In a second step of these embodiments, when the first drive rod 143b and the second drive rod 145b are advanced by driving the linear drivers 147b and 149b of the front feeders 131b, the pair of grippers 133b advance by mutual joint motion between the links in the state of gripping the catheter, and the pair of grippers 133b are located in a forward position and insert the catheter into a blood vessel of a patient.

In this second step, when the first drive rod 143a and the second drive rod 145a are moved backward by driving the linear drivers 147a and 149a of the rear feeders 131a, the pair of grippers 133a retract by mutual joint motion between the links in the state of not gripping the catheter, and the pair of grippers 133a are located in a backward position. Accordingly, in these embodiments, the catheter is advanced a predetermined distance by the front feeders 31b and inserted into the blood vessel of the patient, without being disturbed by the rear feeders 31a.

In a third step of these embodiments, when the second drive rod 145b is moved backward by driving the second linear drivers_149b connected to the second drive rod 145b of the front feeders 131b, the pair of grippers 133b retract a predetermined distance by mutual joint motion between the links, and the pair of grippers 133b are located in a grip release position where the grippers 133b release the grip on the catheter.

In this third step, when the second drive rod 145a is advanced by driving the second linear drivers 149a connected to the second drive rod 145a of the rear feeders 131a, the pair of grippers 133a advance a predetermined distance by mutual joint motion between the links, and the pair of grippers 133a are located in a grip position where the grippers 133a grip the catheter.

In a fourth step of these embodiments, when the first drive rod 143b and the second drive rod 145b are moved backward by driving the linear drivers 147b and 149b of the front feeders 131b, the pair of grippers 133b retract by mutual joint motion between the links in the state of not gripping the catheter, and the pair of grippers 133b are located in the backward position.

In this fourth step, when the first drive rod 143a and the second drive rod 145a are advanced by driving the linear drivers 147a and 149a of the rear feeders 131a, the pair of grippers 133a advance by mutual joint motion between the links in the state of gripping the catheter, and the pair of grippers 133a are located in a forward position. Accordingly, in these embodiments, the catheter is advanced a predetermined distance by the rear feeders 31a and inserted into the blood vessel of the patient, without being disturbed by the front feeders 31b.

In a fifth step of these embodiments, when the second drive rod 145b is advanced by driving the second linear drivers_149b connected to the second drive rod 145b of the front feeders 131b, the pair of grippers 133b advance a predetermined distance by mutual joint motion between the links, and the pair of grippers 133b are located in the grip position where the grippers 133b grip the catheter.

In this fifth step, when the second drive rod 145a is moved backward by driving the second linear drivers_149a connected to the second drive rod 145a of the rear feeders 131a, the pair of grippers 133a retract a predetermined distance by mutual joint motion between the links, and the pair of grippers 133a are located in a grip release position where the grippers 133a release the grip on the catheter.

When the fifth step is completed as described above, the catheter delivery device returns to the second step and repeatedly performs the second to fifth steps. Accordingly, in these embodiments, the catheter delivery device automatically feeds and inserts the catheter into the blood vessel of the patient while mutually organically moving the pair of feeders 131a and 31b. Furthermore, in these embodiments, the catheter is always gripped by either the pair of grippers 133b of the front feeders 131b or the pair of grippers 133a of the rear feeders 131a.

Accordingly, in these embodiments, the pair of feeders 131a and 131b operate to mutually organically being moved in one of the grip position where the grippers 133a and 133b grip the catheter, the forward position where the grippers 133a and 133b advance in the state of gripping the catheter, the grip release position where the grippers 133a and 133b release the grip on the catheter, and the backward position where the grippers 133a and 133b retract in the state in which the grippers 133a and 133b release the grip on the catheter, thereby accurately feeding the catheter, allowing the depth of the catheter inserted to be accurately identified, and improving the accuracy of the catheterization.

Figure 10A:
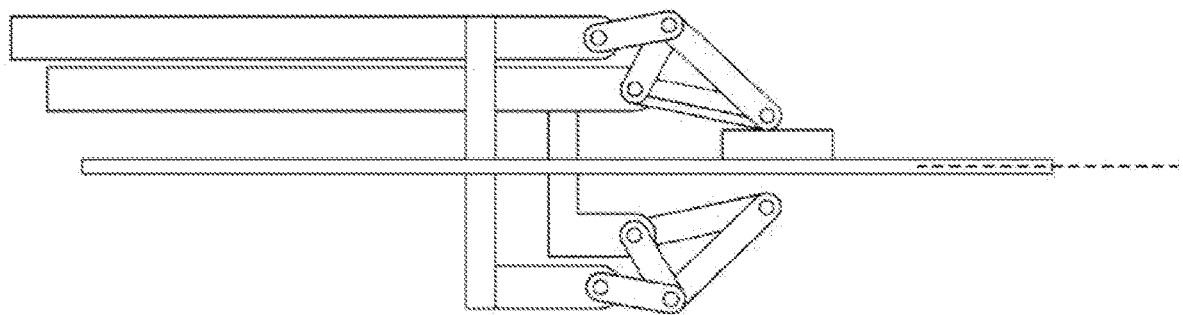
FIGS. 10A and 10B are schematic diagrams illustrating interpretation of a driving relationship of one gripper of the pair of feeders shown in FIG. 9.
Figure 10B:
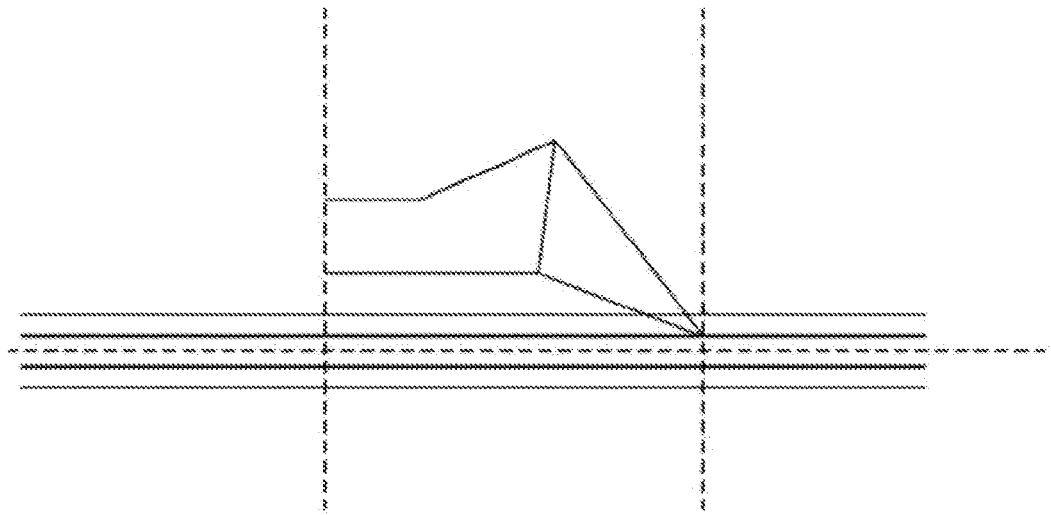

FIGS. 10A and 10B are schematic diagrams illustrating interpretation of a driving relationship of one gripper of the pair of feeders shown in FIG. 9.

It can be seen that both the Y-direction position $Y_e$ of a rubber pad, for example, the gripper for an operation of gripping a catheter and the position $X_e$ for a forward movement and a backward movement of the gripper can be independently controlled as illustrated in FIG. 10.

Figure 11A:
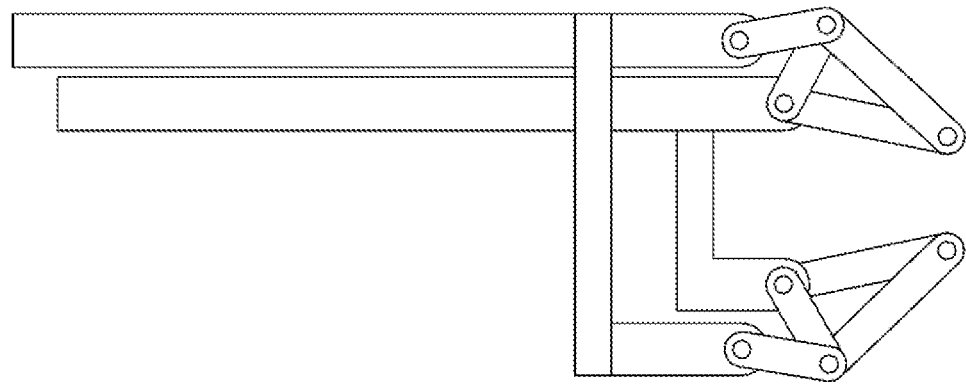
FIGS. 11A and 11B are views illustrating a result obtained by performing simulation of the interpretation result shown in FIGS. 10A and 10B.
Figure 11B:
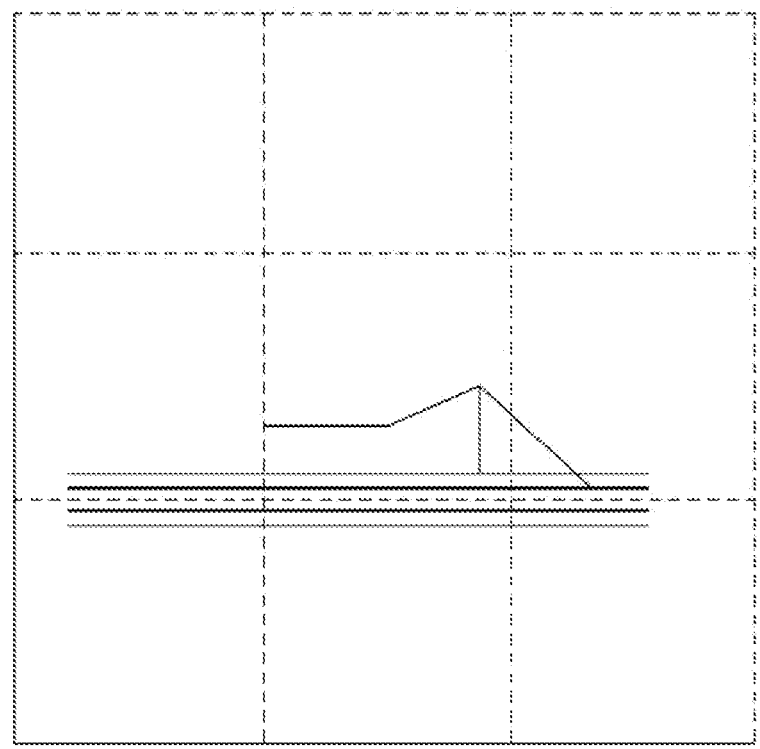

FIGS. 11A and 11B are a view illustrating a result obtained by performing simulation of the interpretation result of FIGS. 10A and 10B.

The feeders 131a for driving the grippers according to the other some embodiments of the present disclosure is illustrated in FIG. 11A. The pair of feeders 131a and 131b are provided as illustrated in FIG. 9 by extending the feeders 131a, and when the pair of feeders 131a and 131b are alternately moved mutually organically as in the detailed description of the process of feeding the catheter, catheterization may be performed as if a person inserts a catheter into a blood vessel of a patient by alternately using the person's both hands. Furthermore, the grippers 133a and 133b of the respective feeders 131a and 131b completely grip the catheter through a wide surface like fingers of a person, thereby easily transmitting a force when feeding and rotating the catheter.

Figure 12:
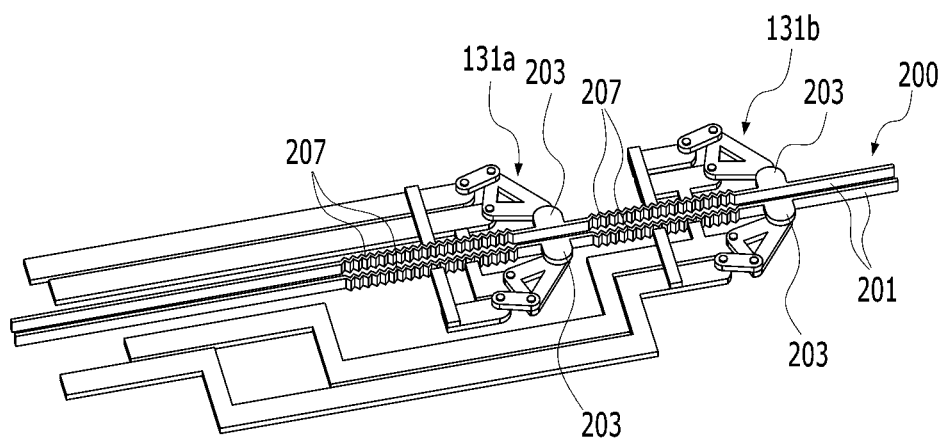
FIG. 12 is a view illustrating a state in which a gripper according to some embodiments of the present disclosure is attached to the pair of feeders shown in FIG. 9.

FIG. 12 illustrates a gripper according to some embodiments of the present disclosure.

As illustrated in FIG. 12, the gripper 200 according to some embodiments of the present disclosure is attached to, for example, the pair of feeders 131a and 131b.

In these embodiments, the gripper 200 includes a pair of bands 201 and corrugated portions 207.

The pair of bands 201 have a strap shape with a predetermined length. The pair of bands 201 are arranged along a delivery path of a catheter to face each other with the catheter therebetween and partly surround the catheter. Furthermore, the pair of bands 201 include support parts 203, and the gripper links (not illustrated in the figures of the present disclosure) of the pair of feeders 131a and 131b are brought into contact with, or separated from, the support parts 203.

The corrugated portions 207 are provided on regions of the bands 201 other than the support parts 203. The corrugated portions 207 have a continuous wave form so as to be expanded or contracted along the delivery direction of the catheter, for example, the lengthwise direction of the bands 201.

Accordingly, in these embodiments, the gripper 200 prevents the catheter being inserted into a body of a patient from being contaminated by an external environment, thereby enabling the catheter to be inserted in a sanitary way. The gripper 200 according to these embodiments may include rubber, silicone, or vinyl material and may be used for single-patient use.

Further, the gripper 200 according to these embodiments may be pivotally coupled with the gripper links. In some embodiments, the pivotally coupled gripper has a shape that can be covered with a pad.

Figure 13:
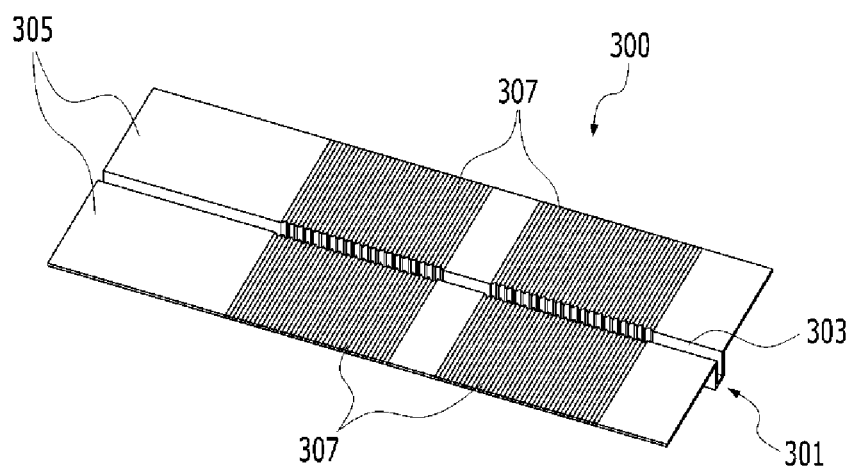
FIG. 13 is a perspective view of a gripper according to some embodiments of the present disclosure.

FIG. 13 illustrates a gripper according to some embodiments of the present disclosure.

In these embodiments illustrated in FIG. 13, the gripper 300 includes a catheter insertion part 301, a pair of cover plates 305, and corrugated portions 307.

The catheter insertion part 301 has a rectangular cross-section that is open at one side. The open region of the catheter insertion part 301 forms an insertion groove 303 into which a catheter is inserted. Furthermore, although not illustrated in the figures of the present disclosure, gripper links of a pair of feeders are brought into contact with, or separated from, the catheter insertion part 301.

The pair of cover plates 305 on opposite sides of the catheter insertion part 301 laterally extend with respect to the delivery path of the catheter and are disposed to face each other to cover the body 11 of the catheter delivery device.

The corrugated portions 307 are formed on the catheter insertion part 301 and the pair of cover plates 305 other than the regions on which the gripper links (not illustrated in the figures of the present disclosure) are supported. The corrugated portions 207 have a continuous wave form so as to be expanded or contracted along the delivery direction of the catheter, for example, the lengthwise direction of the catheter insertion part 301 and the pair of cover plates 305.

Accordingly, in these embodiments, the gripper 300 prevents the catheter being inserted into a body of a patient from being contaminated by an external environment, thereby enabling the catheter to be inserted in a sanitary way. Also, the gripper 300 in these embodiments reduces contamination of the body 11 by foreign substances attached to the catheter when the catheter is removed from the body of the patient. The gripper 300 in these embodiments may include rubber, silicone, or vinyl material and may be used for single-patient use.

The gripper 300 in these embodiments may be pivotally coupled with the gripper links. Furthermore, the pivotally coupled gripper may have a shape that can be covered with a pad.

Although the catheter delivery device that feeds one catheter has been described in the above-described embodiments, the inventive concept is not limited thereto, and a catheter delivery device that feeds a plurality of catheters may be implemented without departing from the scope of the inventive concept.

Furthermore, although the process of inserting the catheter into the blood vessel of the patient has been described in the above-described embodiments, the inventive concept is not limited thereto, and the catheter may be automatically smoothly removed by changing the operation process of the feeders such that the catheter is extracted from the blood vessel of the patient in the state in which the grippers of any one of the pair of feeders grip the catheter.

In addition, the catheter delivery device according to the inventive concept may be provided as one of some components including a steering drivers that remotely controls the curvature of a bending section of a catheter and a master system for haptic corresponding to a user input, and insertion of the catheter into a blood vessel of a patient may be remotely controlled through the master system.

According to the inventive concept, the drive mechanism for a catheter that is inserted into a blood vessel of a patient is improved, thereby easily inserting and removing the catheter, accurately identifying the depth of the catheter inserted, and improving the accuracy of catheterization.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A catheter delivery device comprising:
   a body plate comprising an upper surface, on which a delivery path of a catheter is configured;
   a pair of feeders comprising:
   grippers located on the upper surface of the body plate, and configured to grip and release the catheter; and
   a pair of threaded shafts located on the upper surface of the body plate and configured to control the pair of feeders along the delivery path,
   wherein the pair of feeders are configured to move
   from a grip position where the grippers grip the catheter to a forward position where the grippers advance in a state of gripping the catheter,
   from the forward position to a grip release position where the grippers release the catheter,
   from the grip release position to a backward position where the grippers retract in a state of releasing a grip on the catheter, and
   from the backward position to the grip position; and
   a rotator configured to rotate the catheter gripped by the feeders,
   wherein the rotator comprises a drive motor attached to a bottom surface of the body plate and configured to rotate the body plate.

2. The catheter delivery device of claim 1, wherein the grippers of the pair of feeders are arranged with an interval therebetween along the delivery path of the catheter.

3. The catheter delivery device of claim 1, wherein the feeders include:
   the grippers paired with each other and disposed on opposite sides of the catheter to face each other;
   a pair of gripper links pivotally coupled to the pair of grippers;
   a pair of first links pivotally coupled to the pair of gripper links;
   a pair of second links pivotally coupled to the pair of first links;
   a first movable block to which the pair of gripper links and the pair of first links are pivotally coupled;

a second movable block to which the pair of second links are pivotally coupled;

the pair of threaded shafts threaded into the first movable block and the second movable block to perform screw motion, and configured to deliver the first movable block and the second movable block along the delivery path; and a pair of threaded shaft drive motors configured to rotate the pair of threaded shafts in clockwise direction or counterclockwise direction.

4. The catheter delivery device of claim 3, wherein the pair of threaded shafts are configured to rectilinearly reciprocate the first movable block and the second movable block along the delivery path.

5. The catheter delivery device of claim 3, wherein the grippers include:

a pair of bands arranged along the delivery path to face each other with the catheter therebetween, and configured to partly surround the catheter, the pair of bands having a support part that the gripper links of the pair of feeders are brought into contact with or separated from; and a corrugated portion provided on a region of the bands other than the support part and configured to expand or contract along a direction in which the catheter moves.

6. The catheter delivery device of claim 3, wherein the grippers include:

a catheter insertion part configured to form an insertion groove into which the catheter is inserted, wherein the gripper links of the pair of feeders are brought into contact with or separated from the catheter insertion part;

a pair of cover plates on opposite sides of the catheter insertion part, wherein the pair of cover plates extend perpendicular to the delivery path of the catheter and are disposed to face each other to cover the body plate; and a corrugated portion provided on the catheter insertion part and the pair of cover plates other than regions on which the gripper links are supported, wherein the corrugated portion expands or contracts along a direction in which the catheter moves.

7. The catheter delivery device of claim 3, wherein the threaded shafts include a threaded shaft portion on which an external male thread for transmitting a rotational force is formed along a lengthwise direction and a sliding rod portion for linear motion.

8. The catheter delivery device of claim 3, wherein a pair of threaded shaft supports configured to rotatably support the threaded shafts of the pair of feeders are formed on one side of the upper surface of the body plate, and wherein a pair of branches having a circular arc shape and protruding upward from the body plate to face each other are formed on an opposite side of the upper surface of the body plate.

9. The catheter delivery device of claim 8, wherein the pair of branches are located adjacent to the rotator, and end portions of the pair of branches are connected by a connecting plate, and wherein a catheter mounting hole in which the catheter is movably mounted is formed through the connecting plate.

10. The catheter delivery device of claim 3, wherein a block receiving portion in which the first movable block is partly received is concavely formed in a central region of the second movable block.

11. The catheter delivery device of claim 1, wherein the feeders include:

the grippers paired with each other and disposed on opposite sides of the catheter to face each other;

a pair of first gripper links pivotally coupled to the pair of grippers;

a pair of second gripper links pivotally coupled to the pair of grippers while forming an angle with the pair of first gripper links;

a pair of connecting links pivotally coupled to the pair of first gripper links and the pair of second gripper links to form a triangular shape together with the pair of first gripper links and the pair of second gripper links;

a pair of auxiliary links pivotally coupled to the pair of connecting links and the pair of second gripper links;

a first drive rod pivotally coupled to the pair of first gripper links and the pair of connecting links;

a second drive rod pivotally coupled to the pair of auxiliary links;

a first linear driver connected to the first drive rod, and configured to move the first drive rod; and a second linear driver connected to the second drive rod, and configured to move the second drive rod.

12. The catheter delivery device of claim 11, wherein the first linear driver and the second linear driver are configured to rectilinearly reciprocate the first drive rod and the second drive rod, respectively.

13. The catheter delivery device of claim 11, wherein the grippers include:

a pair of bands arranged along the delivery path to face each other with the catheter therebetween, and configured to partly surround the catheter, the pair of bands having a support part that the gripper links of the pair of feeders are brought into contact with or separated from; and a corrugated portion provided on a region of the bands other than the support part and configured to expand or contract along a direction in which the catheter moves.

14. The catheter delivery device of claim 11, wherein the grippers include:

a catheter insertion part configured to form an insertion groove into which the catheter is inserted, wherein the gripper links of the pair of feeders are brought into contact with or separated from the catheter insertion part;

a pair of cover plates on opposite sides of the catheter insertion part, wherein the pair of cover plates extend perpendicular to the delivery path of the catheter and are disposed to face each other to cover the body plate; and a corrugated portion provided on the catheter insertion part and the pair of cover plates other than regions on which the gripper links are supported, wherein the corrugated portion expands or contracts along a direction in which the catheter moves.

15. The catheter delivery device of claim 1, wherein the rotator further comprises:

a housing that is rotatable relative to the body plate;

an inner gear having a plurality of gear teeth disposed on a particular portion of an inner circumferential surface of the housing, the plurality of gear teeth being arranged along the inner circumferential surface of the housing; and a pinion configured to be engaged with the gear teeth of the inner gear, and configured to be rotated, and wherein the drive motor is a pinion drive motor configured to rotate the pinion.

16. The catheter delivery device of claim 15, further comprising:
   a plurality of rollers configured to support the body plate from the inner circumferential surface of the housing, and configured to move in rolling contact with the inner circumferential surface of the housing.

17. The catheter delivery device of claim 15, further comprising:
   a fixing part configured to fix the housing to a structure.

18. The catheter delivery device of claim 15, wherein the housing has a cylindrical shape and includes an upper housing and a lower housing vertically divided from each other, and
   wherein one end portion of the upper housing and one end portion of the lower housing are hinged to each other to open or cover a region of the body plate, and an opposite end portion of the upper housing and an opposite end portion of the lower housing are locked by a locking device.

19. The catheter delivery device of claim 1, wherein the grippers have a pad shape configured to closely contact with an outer circumferential surface of the catheter.

\* \* \* \* \*